(12) United States Patent
Boyd et al.

(10) Patent No.: US 9,033,602 B2
(45) Date of Patent: May 19, 2015

(54) TOOTHBRUSH HAVING ORAL CARE FLUID DELIVERY

(75) Inventors: Thomas J. Boyd, Metuchen, NJ (US); John J. Gatzemeyer, Hillsborough, NJ (US); Sharon Kennedy, Randallstown, MD (US); Eduardo J. Jimenez, Manalapan, NJ (US)

(73) Assignee: Colgate-Palmolive Company, New York, NY (US)

( * ) Notice: Subject to any disclaimer, the term of this patent is extended or adjusted under 35 U.S.C. 154(b) by 95 days.

(21) Appl. No.: 14/005,734

(22) PCT Filed: Mar. 28, 2011

(86) PCT No.: PCT/US2011/030139
§ 371 (c)(1),
(2), (4) Date: Sep. 17, 2013

(87) PCT Pub. No.: WO2012/134435
PCT Pub. Date: Oct. 4, 2012

(65) Prior Publication Data
US 2014/0000047 A1    Jan. 2, 2014

(51) Int. Cl.
*A46B 11/00* (2006.01)
*A46B 9/04* (2006.01)

(52) U.S. Cl.
CPC ......... *A46B 11/0037* (2013.01); *A46B 11/0055* (2013.01); *A46B 11/0082* (2013.01); *A46B 2200/1066* (2013.01); *A46B 9/04* (2013.01)

(58) Field of Classification Search
CPC ............. A46B 11/00; A46B 11/001

USPC ............ 401/99, 109, 110, 111, 196, 198, 283
See application file for complete search history.

(56) References Cited

U.S. PATENT DOCUMENTS

| | | |
|---|---|---|
| 1,292,416 A | 1/1919 | Auld |
| 1,798,081 A | 3/1931 | Gordyn, Jr. et al. |
| 1,973,212 A | 9/1934 | Krueger |
| D134,723 S | 9/1942 | Riksheim |
| 2,573,201 A | 10/1951 | Kelley et al. |
| 2,594,721 A | 4/1952 | Beebe |
| 2,637,060 A | 5/1953 | Cowan |
| 2,800,899 A | 7/1957 | Barron |

(Continued)

FOREIGN PATENT DOCUMENTS

| | | |
|---|---|---|
| DE | 90 07 098 | 9/1999 |
| DE | 10035214 | 2/2002 |

(Continued)

OTHER PUBLICATIONS

International Search Report issued in International Application PCT/US2008/051778 mailed Dec. 12, 2008.

(Continued)

*Primary Examiner* — David Walczak
*Assistant Examiner* — Joshua Wiljanen
(74) *Attorney, Agent, or Firm* — Ryan M. Flandro

(57) ABSTRACT

A fluid dispensing toothbrush (100). In one aspect, the toothbrush comprises a body (105) having a reservoir (135) containing an oral care fluid (136) therein, the oral care fluid being delivered to an applicator (132) via capillary action. The toothbrush comprises an actuator (130) for moving either the applicator and/or the reservoir between different positions.

26 Claims, 10 Drawing Sheets

(56) References Cited

U.S. PATENT DOCUMENTS

| | | | |
|---|---|---|---|
| 3,296,642 A | 1/1967 | Aylott | |
| 3,369,543 A | 2/1968 | Ronco | |
| 3,406,694 A | 10/1968 | Odence | |
| 3,749,503 A | 7/1973 | Duerr | |
| 3,910,706 A | 10/1975 | Del Bon | |
| 3,938,897 A | 2/1976 | Craig | |
| 4,023,580 A | 5/1977 | Pieters | |
| 4,088,412 A | 5/1978 | Del Bon | |
| 4,275,750 A | 6/1981 | Clark | |
| 4,296,518 A | 10/1981 | Furrier et al. | |
| 4,585,018 A | 4/1986 | O'Connor | |
| 4,695,177 A | 9/1987 | Kuo | |
| 4,879,781 A | 11/1989 | Desimone | |
| 4,950,095 A | 8/1990 | Picard | |
| 5,017,036 A | 5/1991 | Vidovic | |
| 5,033,898 A | 7/1991 | Williams | |
| 5,062,728 A | 11/1991 | Kuo | |
| 5,096,319 A | 3/1992 | Gueret | |
| 5,098,297 A | 3/1992 | Chari et al. | |
| 5,102,251 A | 4/1992 | Kaufmann | |
| 5,174,814 A * | 12/1992 | Burwell et al. | 106/31.15 |
| D337,659 S | 7/1993 | Lacy | |
| 5,346,324 A | 9/1994 | Kuo | |
| 5,352,052 A | 10/1994 | Kaufmann | |
| 5,476,384 A | 12/1995 | Giuliani et al. | |
| 5,611,687 A | 3/1997 | Wagner | |
| 5,765,573 A | 6/1998 | Gueret | |
| 5,913,632 A | 6/1999 | Persad | |
| 5,941,254 A | 8/1999 | Heler | |
| 6,015,293 A | 1/2000 | Rimkus | |
| 6,089,776 A | 7/2000 | Kaufmann | |
| 6,095,707 A | 8/2000 | Kaufmann | |
| 6,164,858 A | 12/2000 | Kaufmann | |
| 6,183,155 B1 | 2/2001 | Kaufmann | |
| 6,202,247 B1 | 3/2001 | Lorenz, Jr. | |
| 6,205,611 B1 | 3/2001 | Vigil | |
| 6,220,773 B1 | 4/2001 | Wiegner et al. | |
| 6,290,417 B1 | 9/2001 | Kaminski | |
| 6,322,268 B1 | 11/2001 | Kaufmann et al. | |
| 6,371,674 B1 | 4/2002 | Lerner | |
| 6,497,527 B2 | 12/2002 | Kaufmann | |
| 6,669,930 B1 | 12/2003 | Hoic et al. | |
| 6,770,266 B2 | 8/2004 | Santarpia, III et al. | |
| 6,802,097 B2 | 10/2004 | Hafliger et al. | |
| D510,482 S | 10/2005 | Jimenez | |
| 7,003,839 B2 | 2/2006 | Hafliger et al. | |
| 7,044,671 B2 | 5/2006 | Parikh et al. | |
| 7,055,527 B2 | 6/2006 | Tien | |
| 7,059,796 B2 * | 6/2006 | Lewis et al. | 401/107 |
| 7,143,462 B2 | 12/2006 | Hohlbein | |
| 7,172,360 B2 | 2/2007 | McSweeney et al. | |
| 7,237,974 B2 | 7/2007 | Pfenniger et al. | |
| 7,401,373 B2 | 7/2008 | Tybinkowski et al. | |
| 7,557,936 B2 | 7/2009 | Dickinson | |
| 8,398,326 B2 * | 3/2013 | Jimenez et al. | 401/282 |
| 2002/0073496 A1 | 6/2002 | Kim | |
| 2004/0182414 A1 | 9/2004 | Puskas | |
| 2004/0237226 A1 | 12/2004 | Hohlbein et al. | |
| 2004/0255416 A1 | 12/2004 | Hohlbein | |
| 2005/0091769 A1 | 5/2005 | Jimenez et al. | |
| 2005/0191111 A1 * | 9/2005 | Carroll | 401/107 |
| 2005/0217688 A1 | 10/2005 | Liu et al. | |
| 2005/0218033 A1 | 10/2005 | Curtis | |
| 2005/0220530 A1 | 10/2005 | Carmona | |
| 2005/0233279 A1 | 10/2005 | Zeh et al. | |
| 2007/0101525 A1 | 5/2007 | Hohlbein | |
| 2008/0014010 A1 | 1/2008 | Bartschi et al. | |
| 2008/0274066 A1 | 11/2008 | Montgomery | |
| 2009/0245920 A1 * | 10/2009 | Jeon | 401/109 |
| 2011/0041275 A1 | 2/2011 | Gatzemeyer et al. | |
| 2013/0309629 A1 * | 11/2013 | Jimenez et al. | 433/82 |
| 2014/0119809 A1 * | 5/2014 | Worthington et al. | 401/283 |

FOREIGN PATENT DOCUMENTS

| | | |
|---|---|---|
| EP | 1639913 | 3/2006 |
| GB | 1 470 268 | 4/1977 |
| GB | 2394653 | 5/2004 |
| GB | 2430146 | 3/2007 |
| WO | WO 2007/073917 | 7/2007 |
| WO | WO 2011/106017 | 9/2011 |

OTHER PUBLICATIONS

International Search Report and the Written Opinion issued in International Application PCT/US2011/030139 mailed Dec. 23, 2011.

* cited by examiner

TOOTHBRUSH HAVING ORAL CARE FLUID DELIVERY

CROSS-REFERENCE TO RELATED PATENT APPLICATIONS

The present application is a U.S. national stage application under 35 U.S.C. §371 of PCT Application No. PCT/US2011/030139, filed Mar. 28, 2011, the entirety of which is incorporated herein by reference.

FIELD OF THE INVENTION

The present invention relates generally to toothbrushes, and more specifically to toothbrushes having oral care fluid delivery.

BACKGROUND OF THE INVENTION

Toothbrushes are typically used by applying toothpaste to a bristle section followed by brushing regions of the oral cavity, e.g., the teeth, tongue and/or gums. Some toothbrushes have been equipped with fluid reservoirs and systems for delivering auxiliary oral care fluids, such as whitening agents, breath freshening agents and others to a user's oral cavity, in addition to dentifrice. However, in known toothbrushes having fluid delivery capabilities, an applicator containing the oral care fluid is permanently exposed to the external environment. Such oral care implements do not provide adequate sanitary storage between oral care sessions and/or have a tendency to expend the oral care fluid within the reservoir due to excessive evaporation. Thus, a need exists for a toothbrush having an oral care fluid delivery system that protects the applicator from external contaminants in between uses and/or prevents unnecessary loss of the oral care fluid from the reservoir due to excessive evaporation. Furthermore, an additional need exists for a toothbrush having an oral care fluid delivery system that can achieve controlled dosing via capillary action.

BRIEF SUMMARY OF THE INVENTION

Exemplary embodiments of the invention are directed to toothbrushes that have a fluid delivery system. The inventive toothbrush comprises a body having a reservoir containing an oral care fluid therein, the oral care fluid being delivered to an applicator via capillary action. The toothbrush comprises an actuator for moving either the applicator and/or the reservoir between different positions.

In one embodiment, the invention can be a toothbrush having a longitudinal axis comprising: a body comprising a handle, a head coupled to a distal end of the handle, and an internal reservoir containing an oral care fluid; a channel in the body extending from the reservoir to an opening in an outer surface of the body; an applicator comprising a capillary material; an actuator operably coupled to the applicator to move the applicator between: (1) a protracted position in which a portion of the applicator protrudes from the opening; and (2) a retracted position in which the portion of the applicator is retracted into the channel via the opening; and wherein the applicator is in fluid communication with the oral care fluid within the reservoir in both the protracted position and the retracted position so that the oral care fluid is delivered to the applicator via capillary action.

In another embodiment, the invention can be a toothbrush having a longitudinal axis comprising: a body comprising a handle, a head coupled to a distal end of the handle, and an internal reservoir containing an oral care fluid; a channel in the body extending from the reservoir to an opening in an outer surface of the body; an applicator comprising a capillary material; an actuator operably coupled to the applicator to move the applicator between: (1) a protracted position in which a portion of the applicator protrudes from the opening; and (2) a retracted position in which the portion of the applicator is retracted into the channel via the opening; and wherein the applicator is in fluid communication with the oral care fluid within the reservoir in the retracted position so that the oral care fluid is delivered to the applicator via capillary action and removed from fluid communication with the oral care fluid within the reservoir in the protracted position.

In yet another embodiment, the invention can be a toothbrush having a longitudinal axis comprising: a body comprising a handle, a head coupled to a distal end of the handle, and an internal cavity; a reservoir housing disposed within the internal cavity of the body and containing an oral care fluid; an applicator comprising a capillary material affixed to an outer surface of the body; a channel in the body extending from the internal cavity to the applicator; an actuator operably coupled to the reservoir housing for moving the reservoir housing within the internal cavity between: (1) a first position in which the applicator is removed from fluid communication with the oral care fluid within the reservoir housing; and (2) a second position in which the applicator is in fluid communication with the oral care fluid within the reservoir housing so that the oral care fluid is delivered to the applicator via capillary action.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE INVENTION

Figure 1:
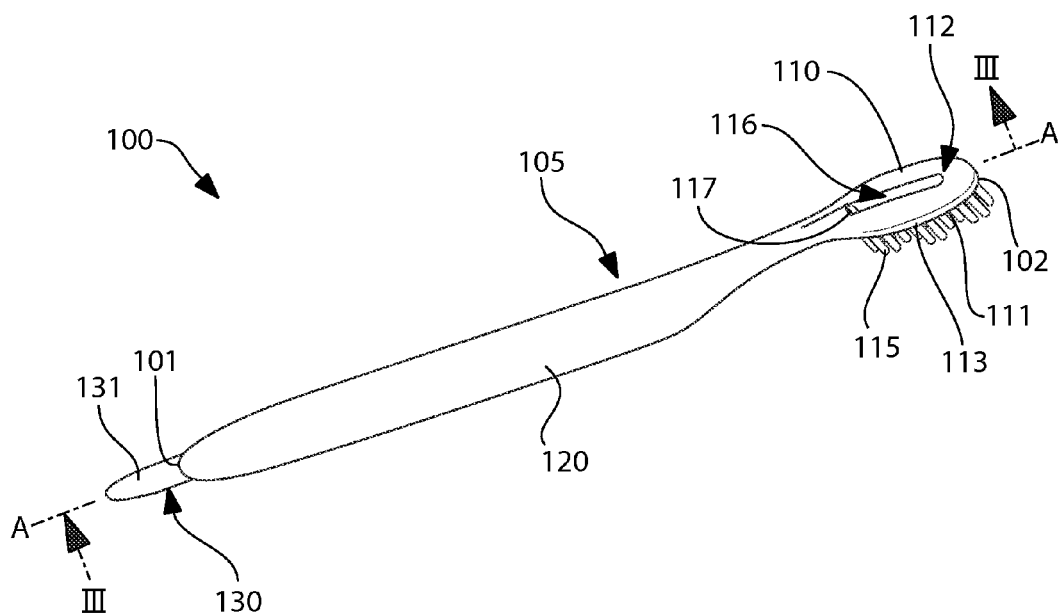
FIG. 1 is a rear perspective view of a toothbrush according to a first embodiment of the present invention, wherein the applicator is in a retracted position.

The following description of the preferred embodiment(s) is merely exemplary in nature and is in no way intended to limit the invention, its application, or uses.

The description of illustrative embodiments according to principles of the present invention is intended to be read in connection with the accompanying drawings, which are to be considered part of the entire written description. In the description of the exemplary embodiments of the invention disclosed herein, any reference to direction or orientation is merely intended for convenience of description and is not intended in any way to limit the scope of the present invention. Relative terms such as "lower," "upper," "horizontal," "vertical," "above," "below," "up," "down," "left," "right," "top," "bottom," "front" and "rear" as well as derivatives thereof (e.g., "horizontally," "downwardly," "upwardly," etc.) should be construed to refer to the orientation as then described or as shown in the drawing under discussion. These relative terms are for convenience of description only and do not require that the apparatus be constructed or operated in a particular orientation unless explicitly indicated as such. Terms such as "attached," "affixed," "connected," "coupled," "interconnected," "secured" and similar refer to a relationship wherein structures are secured or attached to one another either directly or indirectly through intervening structures, as well as both movable or rigid attachments or relationships, unless expressly described otherwise. Moreover, the features and benefits of the invention are described by reference to the exemplary embodiments illustrated herein. Accordingly, the invention expressly should not be limited to such exemplary embodiments, even if indicated as being preferred. The discussion herein describes and illustrates some possible non-limiting combinations of features that may exist alone or in other combinations of features. The scope of the invention is defined by the claims appended hereto.

Figure 2:
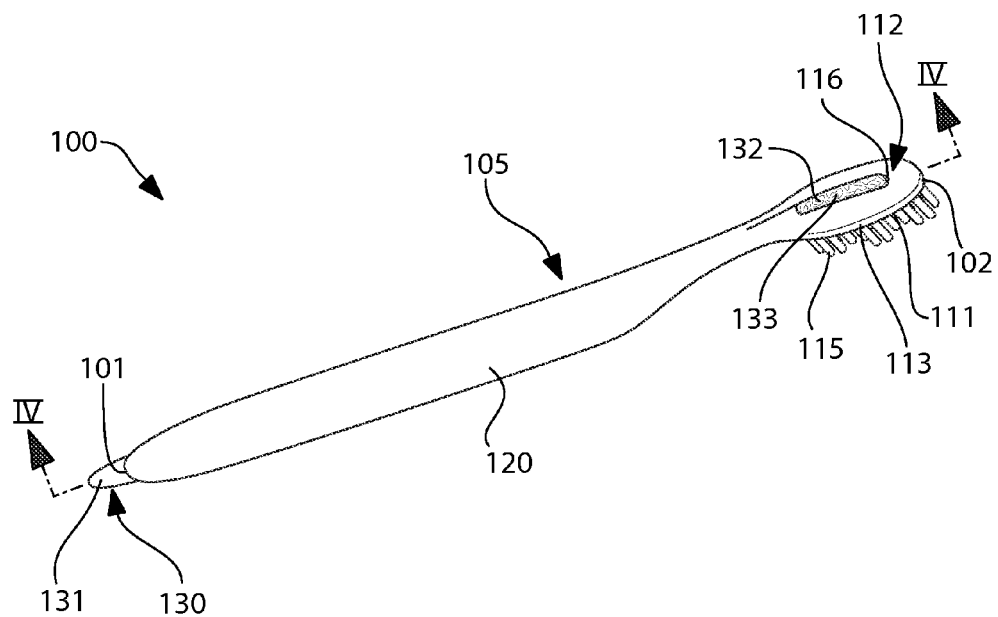
FIG. 2 is a rear perspective view of the toothbrush of FIG. 1 wherein the applicator is in a protracted position.

Referring to FIGS. 1 and 2, a toothbrush 100 in accordance with one embodiment of the present invention is illustrated. In the exemplified embodiments disclosed herein, the invention is illustrated and described in the form of a manual toothbrush. However, the invention is not so limited in all embodiments, and the oral care fluid delivery system and techniques described herein can be incorporated into other oral care implements as desired, including without limitation a powered toothbrush, an interdental device, a soft tissue cleanser or any other type of oral care implement as is known in the art.

The toothbrush 100 extends from a proximal end 101 to a distal end 102 along a longitudinal axis A-A. The toothbrush 100 generally comprises a body 105 having a head 110 and a handle 120. The body 105 is constructed of a material having suitable rigidity for handling of the toothbrush 100 and being sufficiently impervious to fluids so that oral care fluid can be stored within an internal reservoir (discussed below). Suitable material include hard plastics, such as polyethylene, polypropylene (PP), polyamide, polyester, cellulosics, SAN, acrylic, ABS or any other of the commonly known thermoplastics used in toothbrush manufacture.

The head 110 is coupled to a distal end of the handle 120. In the exemplary embodiment, the head 110 and the handle 120 are integrally formed as a single unitary structure using a molding, milling, machining or other suitable process. However, in other embodiments the handle 120 and the head 110 may be formed as separate components which are operably connected at a later stage of the manufacturing process by any suitable technique known in the art, including without limitation thermal or ultrasonic welding, a tight-fit assembly, a coupling sleeve, threaded engagement, adhesion, or fasteners. Whether the head 110 and the handle 120 are of a unitary or multi-piece construction (including connection techniques) is not limiting of the present invention, unless specifically claimed. In some embodiments of the invention, the head 110 may be detachable (and replaceable) from the handle 120 using techniques known in the art.

The head 110 comprises a front surface 111, a rear surface 112 and a peripheral side surface 113. The front surface 111 and the rear surface 112 of the head 110 can take on a wide variety of shapes and contours, none of which are limiting of the present invention. For example, the front and rear surfaces 111, 112 can be planar, contoured or combinations thereof. Moreover, if desired, the rear surface 112 of the head 110 may also comprise additional structures (in addition to the applicator 132) for oral cleaning, such as an elastomeric soft tissue cleanser. An example of a suitable elastomeric soft tissue cleanser is disclosed in U.S. Pat. No. 7,143,462, issued Dec. 5, 2006 to the assignee of the present application, the entirety of which is hereby incorporated by reference. Furthermore, while the head 110 is normally widened relative to the neck of the handle 120, it could in some constructions simply be a continuous extension or narrowing of the handle 120.

The head 110 also comprises a plurality of tooth cleaning elements 115 extending from the front surface 111. The tooth cleaning elements 115 are generically illustrated as a plurality of tufts of bristles. However, the invention is in no way limited by the configuration or material of the tooth cleaning elements 115. Furthermore, while the plurality of tooth cleaning elements 115 are particularly suited for brushing and/or polishing teeth, the plurality of tooth cleaning elements 115 can also be used to clean oral soft tissue, such as a tongue, gums, or cheeks instead of or in addition to teeth.

As used herein, the term "tooth cleaning elements" is used in a generic sense to refer to any structure that can be used to clean, polish or wipe the teeth and/or soft oral tissue (e.g. tongue, cheek, gums, etc.) through relative surface contact. Common examples of "tooth cleaning elements" include, without limitation, bristle tufts, filament bristles, fiber bristles, nylon bristles, spiral bristles, rubber bristles, elastomeric protrusions, flexible polymer protrusions, combinations thereof and/or structures containing such materials or combinations. Suitable elastomeric materials include any biocompatible resilient material suitable for uses in an oral hygiene apparatus. To provide optimum comfort as well as cleaning benefits, the elastomeric material of the tooth or soft tissue engaging elements has a hardness property in the range of A8 to A25 Shore hardness. One suitable elastomeric material is styrene-ethylene/butylene-styrene block copolymer (SEBS) manufactured by GLS Corporation. Nevertheless, SEBS material from other manufacturers or other materials within and outside the noted hardness range could be used.

The plurality of tooth cleaning elements 115 can be mounted to the head 110 in any manner known in the art. For example, staples/anchors, in-mold tufting (IMT) or anchor free tufting (AFT) could be used to mount the cleaning elements/tooth engaging elements. In AFT, a plate or membrane is secured to the brush head such as by ultrasonic welding. The bristles extend through the plate or membrane. The free ends of the bristles on one side of the plate or membrane perform the cleaning function. The ends of the bristles on the other side of the plate or membrane are melted together by heat to be anchored in place. Any suitable form of cleaning elements may be used in the broad practice of this invention. Alternatively, the bristles could be mounted to tuft blocks or sections by extending through suitable depressions in the tuft blocks so that the base of the bristles is mounted within or below the tuft block.

The rear surface 112 of the head 110 comprises an opening 117 and a depression 116. As will be discussed in greater detail below with respect to FIGS. 3 and 4, the opening 117 is the termination of a channel 140 in the outer surface 121 of the body 105, the channel 140 forming a passageway into an internal reservoir 135 (see FIGS. 3-4). While the opening 117 is located on the rear surface 112 of the head 110, the invention is not so limited and in certain other embodiments the opening 117 (and the depression 116 if desired) may be formed at other location on the outer surface 121 of the body 105. For example, the opening 117 (and the depression 116 if desired) may be located on the handle 120 or the neck, or even on the front surface 111 of the head 110 if desired.

As discussed below with respect to FIGS. 3 and 4, the depression 116 provides a basin in which a portion of the applicator 132 nests when protracted. In the exemplified embodiment, the depression 116 is illustrated as a groove that is elongated in the axial direction (i.e., along the longitudinal axis A-A). However, the invention is not so limited and in certain other embodiments the depression 116 can take on other shapes and orientations. For example, the depression 116 may be a circular depression, an irregularly shaped depression, or a depression that is elongated in the transverse direction. Thus, the invention is not to be limited by the size, shape and/or location of the depression 116, unless specifically claimed. In still other embodiments, the depression 116 may be omitted all together.

As mentioned above, in certain alternate embodiments, the rear surface of the head 112 may further comprise an elastomeric soft tissue cleanser. The elastomeric soft tissue cleanser is preferably constructed of a thermoplastic elastomer and comprises a plurality of tissue engaging elements in the form of projections, such as nubs and/or ridges. When a soft tissue cleanser is disposed on the rear surface 112 of the head 110, the tissue cleanser may be located on the portions of the rear surface 112 of the head 110 adjacent the depression 116. In certain other embodiments, the soft tissue cleanser may cover the depression 166. In such an embodiment, the elastomeric soft tissue cleanser will comprise one or more openings that are in fluid communication with the depression 116. This will allow fluid communication between the oral cavity and the oral care fluid absorbed into the applicator 132 (when the applicator 132 is in the protracted position as discussed below).

The toothbrush 100 further comprises an actuator 130 which, as discussed below, is used to actuate/move either the applicator 132 or the reservoir housing 635 between desired positions. In the exemplified embodiment, the actuator 130 comprises a push member 131 that protrudes from the proximal end 101 of the handle 120 along the longitudinal axis A-A. In the embodiment of FIGS. 1-4, the actuator 130 moves (or actuates) an applicator 132 between a retracted position, shown in FIG. 1, and a protracted position, shown in FIG. 2. The actuator 130 further comprises a resilient member 175 that biases the actuator 130 so that the applicator 132 is in the retracted position. The resilient member 175 is in the form of a coil spring that surrounds a rod portion 176 of the push member 131, thereby biasing the actuator 130 in a second axial direction D2 (FIG. 5A). In other embodiments, the resilient member 175 can be any type of resilient component, including without limitation different types of springs, elastomeric elements, resilient prongs, and/or combinations thereof. As can be seen from a comparison of FIGS. 1 and 2, a larger length/portion of the push member 131 of the actuator 130 protrudes from the proximal end 101 of the handle 120 when the applicator 132 is in the retracted position than when the applicator 132 is in the protracted position. Thus, in the exemplified embodiment, the actuator 130 itself can be considered to have a retracted position and a protracted position that are opposite to those corresponding positions of the applicator 132.

During actuation, the actuator 130 is moved in an axial direction along the longitudinal axis A-A to move the applicator 132 between the retracted and protracted positions. Specifically, movement of the push member 131 in a first axial direction D1 (FIG. 5A) moves the applicator 132 from the retracted position to the protracted position. In the exemplified embodiment, the first axial direction D1 is a direction traveling along the longitudinal axis A-A from the proximal end 101 to the distal end 102 of the toothbrush 100. Moreover, movement of the push member 131 in a second axial direction D2 (FIG. 5A) that is opposite the first axial direction D1 moves the applicator 132 from the protracted position back to the retracted position. In the exemplified embodiment, the second axial direction D2 is the direction traveling along the longitudinal axis A-A from the distal end 102 to the proximal end 101 of the toothbrush 100. Correspondingly, the applicator 132 is translated in the first axial direction D1 when moved from the retracted position to the protracted position and in the second axial direction when moved from the protracted position back to the retracted position.

As will be described in more detail below with reference to FIGS. 3 and 4, the actuator 130 is operably coupled to the applicator 132. Thus, actuation of the actuator 130 moves the applicator 132 between the retracted and protracted positions. When the applicator 132 is in the protracted position, at least a portion 133 of the applicator 132 protrudes from the opening 117 so that the applicator can be brought into contact with the desired oral surface to deliver the oral care fluid. When the applicator 132 is in the retracted position, the portion 133 of the applicator 132 is withdrawn within the opening 117 and thus nests within the channel 140, thereby providing a storage position in which the applicator 132 is protected from excess evaporation and contamination during periods of non-use.

In the exemplified embodiment, the portion 133 of the applicator 132 also extends into and nests within the depression 116 when the applicator 132 is in the protracted position. Due to the locations of the opening 117 on the head 110, the applicator 132 is adjacent the rear surface 112 of the head 110 when the applicator 132 is in the protracted position in the exemplified embodiment. Moreover, when the actuator 130 is in the protracted position and at least a portion of the applicator 132 is disposed in the depression 116 as illustrated in FIG. 2, the portion 133 of the applicator 132 also protrudes from the rear surface 112 of the head 110. Protrusion of the applicator 132 from the rear surface 112 of the head 110 (or other portion of the outer surface 121 of the body 105) further facilitates us of the applicator 132 to apply an oral care fluid to a user's oral cavity due to its ease of access. In the exemplified embodiment, a first transverse section of the applicator 132 nests within the depression 116 while a second transverse section of the applicator protrudes from the rear surface 112, wherein movement of the applicator 132 during actuation is axial.

Figure 3:
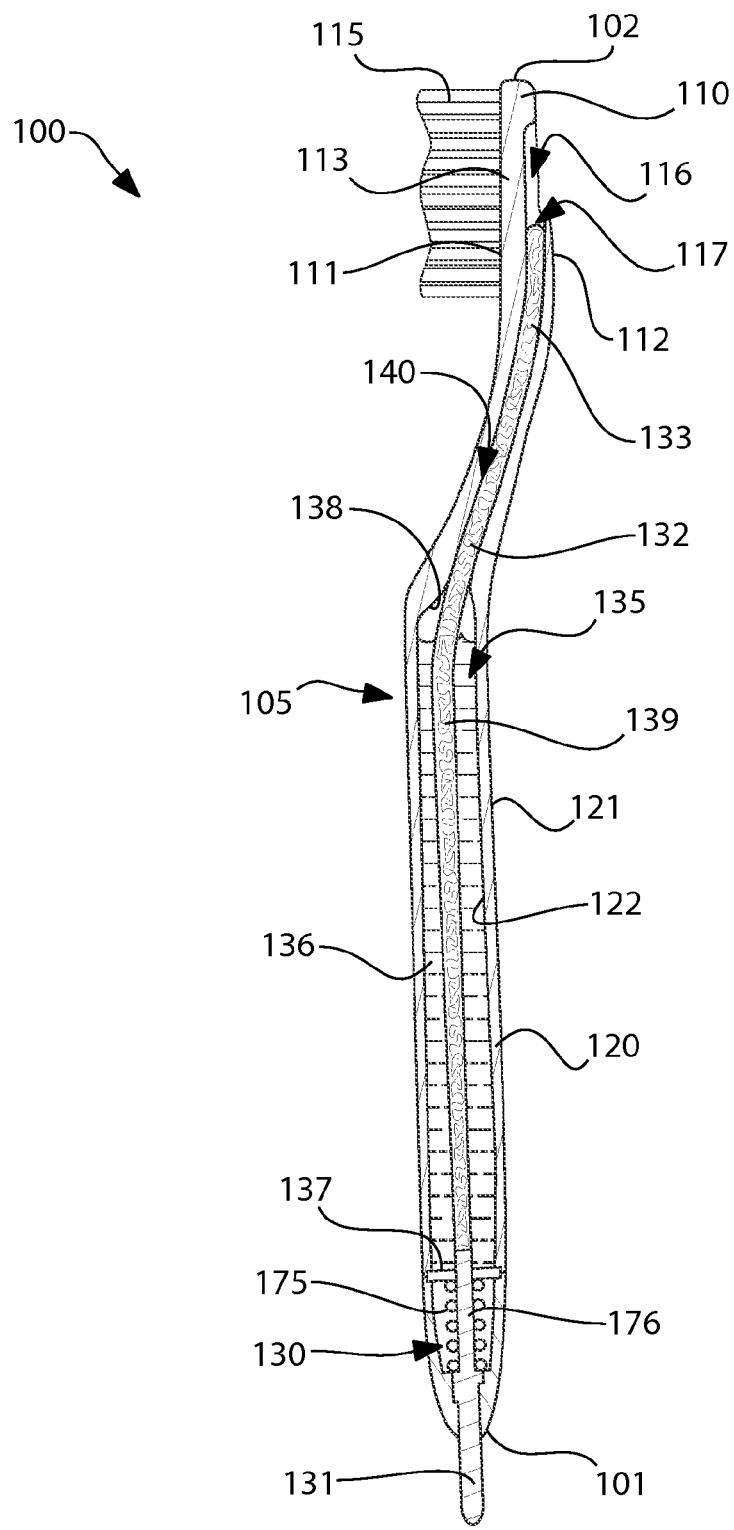
FIG. 3 is a longitudinal cross-sectional view of the toothbrush of FIG. 1 taken along line III-III of FIG. 1.
Figure 4:
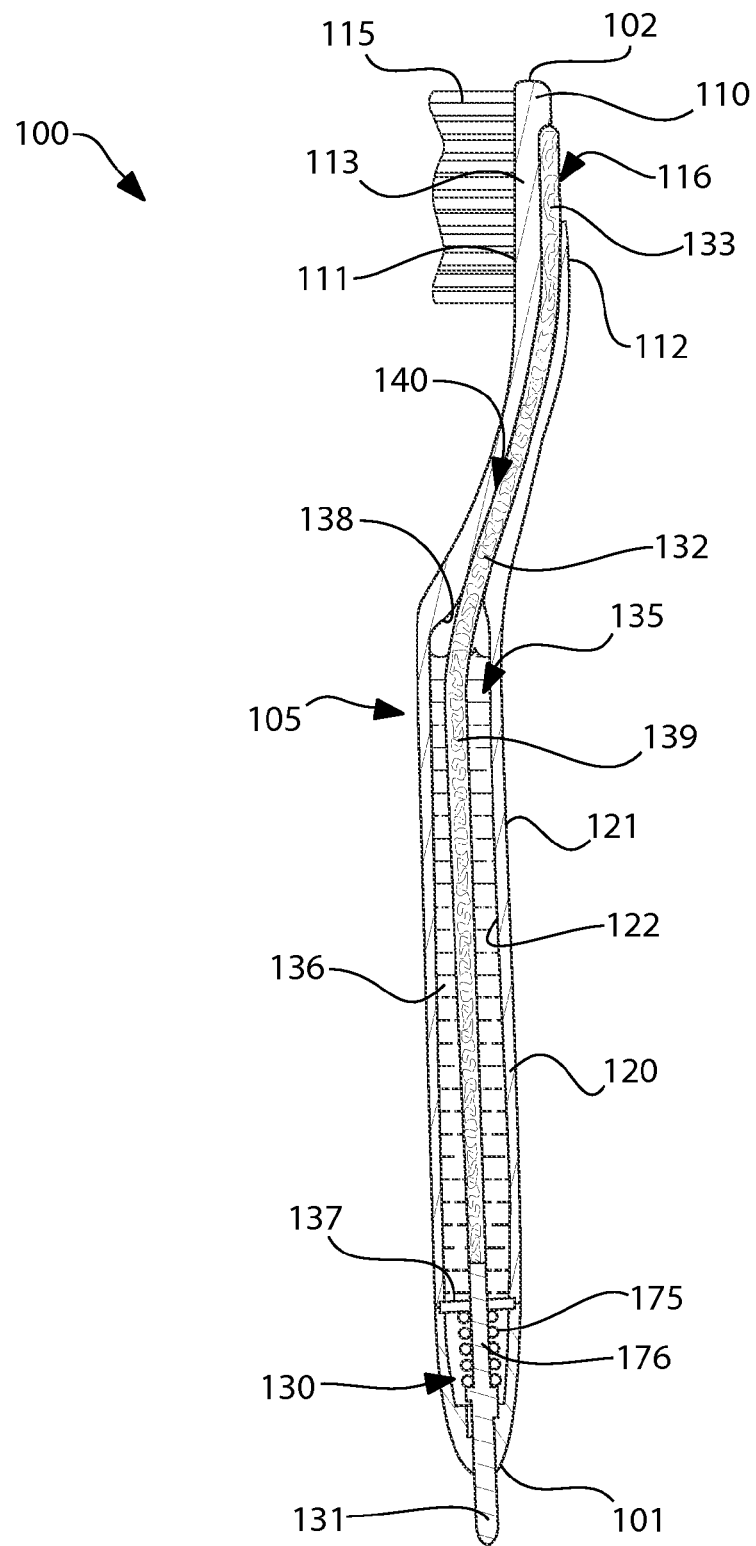
FIG. 4 is a longitudinal cross-sectional view of the toothbrush of FIG. 1 taken along line IV-IV of FIG. 2.
Figures 5A, 5B:
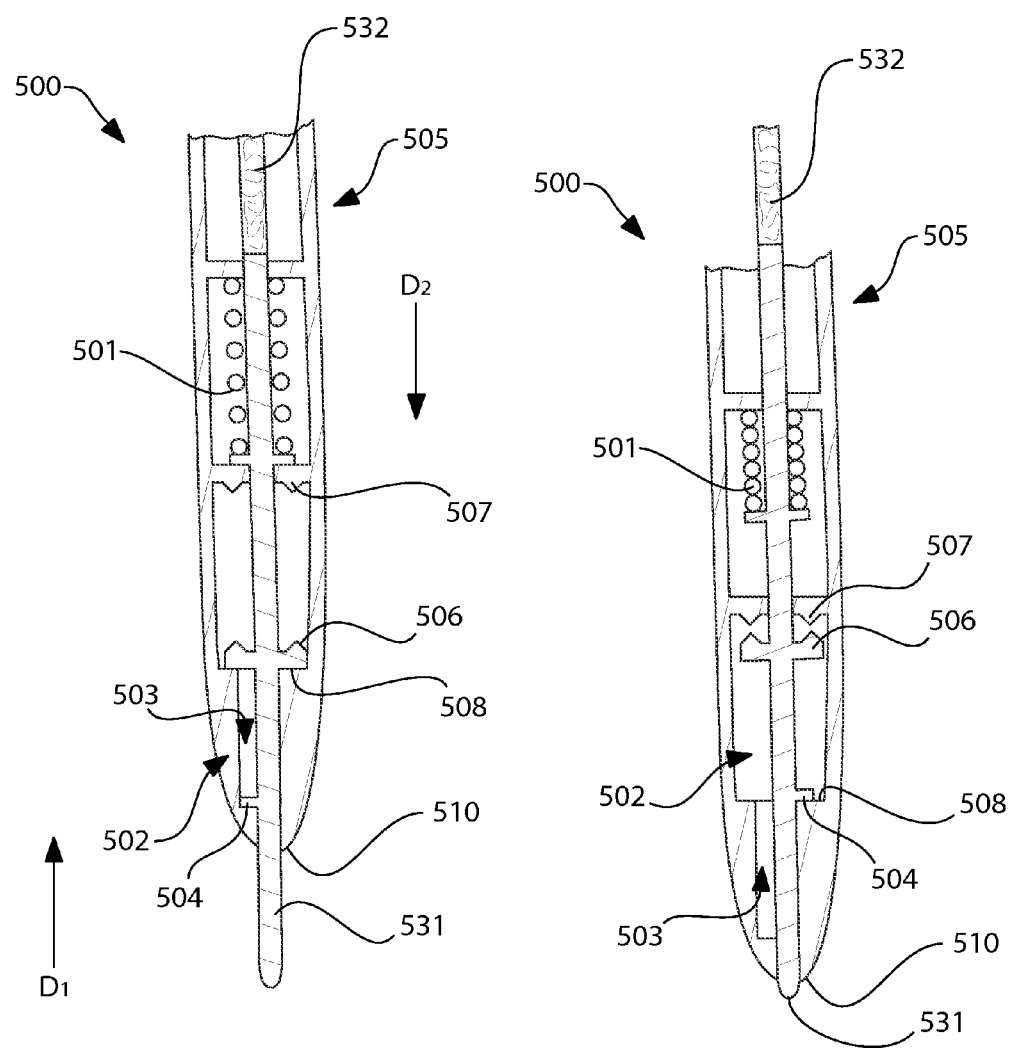
FIG. 5A is a schematic view of an actuator that can be used with the toothbrush of FIG. 1 in a retracted position in accordance with one embodiment of the present invention.
FIG. 5B is a schematic view of the actuator of FIG. 5A in a protracted position.

Referring now to FIGS. 3 and 4, the oral care fluid delivery system of the toothbrush 100 will be further described. The body 105 of the toothbrush 100 comprises an outer surface 121 and an inner surface 122. The rear surface 112 of the head 110 is a portion of the outer surface 121 of the body 105. The inner surface 122 of the body 105 defines an internal reservoir 135 containing an oral care fluid 136 therein. More specifically, the reservoir 135 is defined by the space between a floor 137 of the reservoir 135, a ceiling 138 of the reservoir 135 and the inner surface 122 of the body 105. Thus, the body 105 forms a housing, which contains the reservoir 135 of the oral care fluid 136. In the exemplified embodiment, the reservoir 135 is located within the handle 120. However, in alternate embodiments, the reservoir may be located within the head 110, the neck, the handle 120, and/or combinations thereof.

The oral care fluid 136 provides oral health benefits to a user upon contact with a user's oral cavity. For example, in certain embodiments the oral care fluid 136 is a mouthwash solution that cleans the oral surfaces when applied thereto and provides the user with breath freshening benefits. In other embodiments, the oral care fluid 136 tooth cleaning solution. Of course, the oral care fluid 136 is not to be in any way limiting of the present invention and may include fluids or agents that deliver therapeutic, cosmetic, experiential and/or sensorial benefits to a consumer during an interdental cleaning regimen. Specifically, the oral care fluid can be anti-sensitivity agents, fluoride, tartar protection agents, antibacterial agents, oxidative or whitening agents, enamel strengthening or repair agents, tooth erosion preventing agents, tooth sensitivity ingredients, gum health actives, nutritional ingredients, tartar control or anti-stain ingredients, enzymes, sensate ingredients, flavors or flavor ingredients, breath freshening ingredients, oral malodor reducing agents, anti-attachment agents or sealants, diagnostic solutions, occluding agents, dry mouth relief ingredients, catalysts to enhance the activity of any of these agents, colorants or aesthetic ingredients, arginine bicarbonate, chlorohexidine, triclosan, CPC, zinc oxide and combinations thereof. In certain embodiments, the oral care fluid 136 is free of a dentifrice as the oral care fluid 136 is intended to supplement traditional brushing of the teeth rather than supplant it.

The body 105 of the toothbrush 100 also comprises a channel 140 that extends from the reservoir 135 to the opening 117 in the outer surface 121 of the body 105 (which in the exemplified embodiment is the rear surface 112 of the head 110). The channel 140 forms a passageway from the reservoir 135 to the opening 117. In the exemplified embodiment, the channel 140 is an axial channel extending along the longitudinal axis A-A. In other embodiments, the channel 140 may extend substantially transversely or at an oblique angle to the longitudinal axis A-A. The channel 140 may be linear, curved, and/or combinations thereof. The exact shape and orientation of the channel 140 will be dictated by considerations such as the position of the opening 117 on the body 105, the position of the reservoir 135 within the body 105, and the shape of the body 105.

The applicator 132 is at least partially disposed within the channel 140 and is in fluid communication with the oral care fluid 136 within the reservoir 135. In the exemplified embodiment, the fluid communication between the applicator 132 and the oral care fluid 136 within the reservoir 135 can be considered "indirect fluid communication" due to the existence of a fluid delivery member 139. In certain non-illustrated embodiments, the applicator 132 may be in direct fluid communication with the oral care fluid 136 within the reservoir 135 due to the applicator 132 being positioned closely to the reservoir 135 or the applicator 132 being appropriately sized.

In the exemplified embodiment, the fluid delivery member 139 is an elongated rod constructed of a capillary material. The fluid delivery member 139 is disposed within the channel 140 and extends into the reservoir 135. In the exemplified embodiment, the applicator 132 and the fluid delivery member 139 are integral to one another and of a unitary construct. However, in other embodiments, the fluid delivery member 139 and the applicator can be separate and distinct components and/or structures that are fluidly and/or structurally coupled together when the toothbrush 100 is assembled. Conceptually, the fluid delivery member 139 can be considered as part of the applicator 132, and vice-versa, in certain embodiments.

The fluid delivery member 139 extends between the reservoir 135 and the applicator 132 to effectuate the fluid communication between the applicator 132 and the oral care fluid 136 within the reservoir 135. As will be discussed in more detail below, both the fluid delivery member 139 and the applicator 132 are formed of a capillary material so that the oral care fluid 136 is delivered from the reservoir 135 to the applicator 132 via capillary action. In one embodiment, the delivery of the oral care fluid 136 from the reservoir 135 to the applicator 132 is effectuated solely by capillary action. In a certain embodiment, the oral care fluid 136 is continuously delivered to the applicator 132 (either directly or indirectly) from the reservoir 135 by capillary action. It should be understood that in certain embodiments, the oral care fluid 136 is delivered from the reservoir 135 to the applicator 132 solely by capillary action.

In FIGS. 3 and 4, a simplified actuator 130 is exemplified. However, one specific embodiment of the actuator 130 of the present invention, in the form of a "click-type" actuator, will be described in detail below with reference to FIGS. 5A and 5B. Of course, the invention is not to be limited by the structure of the actuator described in FIGS. 5A and 5B and other methods and structures for moving the applicator 132 between the retracted and protracted positions, as would be known to persons skilled in the art.

As discussed above, the applicator 132 is operably coupled to the actuator 130 so that the applicator 132 moves in response to actuation of the actuator 130. More specifically, actuation of the actuator 130 moves the applicator 132 so that the portion 133 of the applicator 132 extends through the opening 117 and into the depression 116 when the applicator 132 is in the protracted position. The applicator 132 may be directly coupled to the actuator 130, or indirectly coupled to the actuator 130 via the fluid delivery member 139. Furthermore, when the applicator 132 is in the retracted position, the portion 133 of the applicator 132 is withdrawn into the channel 140 through the opening 117 and does not extend into the depression 116. However, the applicator 132 is at least partially disposed within the channel 140 in both the protracted and retracted positions.

As noted above, the applicator 132 and the fluid delivery member 139 are formed of a capillary material that can absorb and/or transport a fluidic material via capillary action. Examples of suitable capillary materials include, without limitation, a porous material, a fibrous material, woven material, non-woven material, a cellular material, a non-cellular materials, or a material comprising one or more capillary channels. When the oral care fluid 135 is delivered to the applicator 132, either directly or indirectly via the fluid delivery member 139, the applicator 132 will absorb the oral care fluid 136 at a rate which decreases over time as the applicator 132 becomes saturated with the oral care fluid 136. When the actuator 130 is in the retracted position, the applicator 132 (either directly or indirectly via the fluid delivery member 139) preferably extends to the floor 137 of the reservoir 135, thereby ensuring that all of the oral care fluid 136 present in the reservoir 135 will be delivered to the applicator 132. In embodiments where the fluid delivery member 139 is not necessary and thus omitted, the applicator 132 is in fluid communication with the oral care fluid 136 within the reservoir 135 in both the protracted and retracted positions so that the oral care fluid 136 is delivered directly to the applicator 132 via capillary action.

In the exemplified embodiment of FIGS. 1-4, the fluid delivery member 139 (and thus the applicator 132) is in fluid communication with the oral care fluid 136 in the reservoir 135 when the applicator 132 is in both the retracted and protracted positions. The applicator 132 extends from an end of the fluid delivery member 139 in the first axial direction D1 (i.e., towards the distal end 102 of the toothbrush 100). Because the applicator 132 and the fluid delivery member 139 are both formed of the capillary material, the oral care fluid 136 that is absorbed by the fluid delivery member 139 within the reservoir will flow to the applicator 132. As noted above, delivery of the oral care fluid 136 from the reservoir 135 to the applicator 132 may be achieved solely by capillary action. The fluid delivery member 139 is in fluid communication with the oral care fluid 136 in the reservoir 135 when the applicator 132 is in both the retracted and protracted positions.

In the exemplified embodiment, the fluid delivery member 139 is affixed to the applicator 132. Thus, actuation of the actuator 130 slides the fluid delivery member 139 within the channel 140, thereby transferring movement to the applicator 132 to move the applicator 132 between the protracted and retracted positions.

When the applicator 132 is in the retracted position (shown in FIG. 3), the applicator 132 is fully contained within the channel 140. As such, no portion of the applicator 132 protrudes from the opening 117 when the applicator 132 is in the retracted position. Of course, in other embodiments, a portion of the applicator 132 may protrude from the opening 117 when the applicator 132 is in the retracted position. By withdrawing the applicator 132 (or at least a portion thereof) into the channel 140, the applicator 132 can be protected from contaminants and undesired evaporation of the oral care fluid 136 during periods of non-use. Thus, the toothbrush 100 achieves a cleaner, more hygienic, more consistent, more effective, and longer lasting delivery of the oral care fluid 136.

When the applicator 132 is in the protracted position (shown in FIG. 4), the portion 133 of the applicator 132 protrudes from the opening 117 and into the depression 116 so as to be exposed. Thus, the oral care fluid 136 which has been absorbed by the applicator 132 (and the portion 133 of the applicator 132) via capillary action will be applied to a user's oral cavity when the head 110 of the oral care implement 100 is positioned within the user's oral cavity. As such, health benefits can be realized by the user by virtue of the oral care fluid 136 being applied to the user's oral cavity.

In certain embodiments, the reservoir 135 can be refillable with the oral care fluid 136. In such embodiments, the body 105 of the oral care implement 100 can include an aperture into the reservoir 135. This aperture can be sealed with a plug or a removable cap. Thus, additional oral care fluid 136 can be introduced into the reservoir 135 as desired. Furthermore, different oral care fluids, such as any of the oral care fluids described above, can be disposed in the reservoir 135 to provide the user with different health benefits.

Referring now to FIGS. 5A and 5B, one embodiment of an actuator 500 will be described in more detail. It should be understood that the actuator 500 can be used as the actuator for any of the embodiments of the toothbrush described herein. Of course, the invention is not limited by the particular actuator used unless specifically recited in the claims and thus, any actuator or method of actuation can be used as would be understood by persons skilled in the art. For example, any type of slide actuator, rotatable actuator, electric actuator, and/or combinations thereof can be used in accordance with the present invention. In addition to illustrating the details of the actuator 500, FIGS. 5A and 5B also illustrate a body 505, an applicator 532 and a push member 531 of a toothbrush 500 for ease of description of the actuator 500. Of course, as described above, a fluid delivery member 309 or other mechanical linkage can be used to transfer the motion of the actuator to the applicator 532.

The actuator 500 comprises a resilient member 501 and an interference lock 502. The resilient member 501 is exemplified as a coil spring. However, the resilient member 501 can be any type of resilient component, including without limitation different types of springs, elastomeric elements, resilient prongs, and/or combinations thereof. In the exemplified embodiment, the resilient member 501 biases the applicator 532 into the retracted position. The applicator 532 is illustrated in the retracted position in FIG. 5A and in the protracted position in FIG. 5B, which should be understood from the description of FIGS. 1-4 above. The resilient member 501 biases the applicator 532 in the second axial direction $D_2$ towards a proximal end 510 of the body 505.

The interference lock 502 comprises a slot 503 formed into the body 505, a flange 504 affixed to the push member 531, a lower cam surface 506 affixed to the push member 531, and an upper cam surface 507 affixed to the body 505. When the applicator 532 is in the retracted position (illustrated in FIG. 5A), the flange 504 is in axial alignment with the slot 503 and is, thus, biased into the slot 503 by the resilient member 501. Furthermore, it should be understood that although the flange 504 is part of the actuator 500 and the slot 503 is part the body 505 in the exemplified embodiment, in certain other embodiments the flange 504 can be formed as part of the body 505 and the slot 503 can be formed as part of the actuator 500.

A description of moving the applicator 532 from the retracted position to the protracted position, and then back to the retracted position will now be undertaken. A user depresses the push member 531 in the first axial direction $D_1$, thereby overcoming the bias force of the resilient member 501 and translating the slide member 531 into the body 505 of the toothbrush 500. During this movement, the flange 504 and the lower cam surface 506 are also translated in the first axial direction D1 until the flange 504 exits the slot 503 and the lower cam surface 506 comes into contact with the upper cam surface 507. The resilient member 501 also becomes compressed at this time. Upon the upper and lower cam surfaces 506, 507 coming into contact with one another, interaction between the cams on the upper and lower cam surfaces 506, 507 causes the push member 531 (along with the flange 504) to rotate relative to the body 505 of the toothbrush 500. As a result of this rotation, the flange 504 is rotated out of axial alignment with the slot 503 (FIG. 5B). At this point, the user can relieve pressing force on the push member 531. The resilient member 501 will then bias (and move) the push member 531 in the second axial direction D2 a small distance until the flange 504 contacts the shoulder 508 of the body 505. The applicator 532 is now in the protracted position. Interference contact between the flange 504 and the shoulder 508 prevents the applicator 532 from being automatically moved back into the retracted position because the push member 532 can move no further in the second axial direction D2. This is considered a single "click" of the actuator 530.

When it is desired to react the applicator 532, the user then reapplies a pressing force to the push member 531, causing a small movement of the push member (including the flange 504 and the lower cam surface 506) in the first axial direction D1 until the upper and lower cam surfaces 506, 507 come into contact with one another again, thereby rotating the push member 531 a second time so that the flange 504 is back in axial alignment with the slot 503. This is the second "click." Because the flange 504 is in alignment with the slot 503, release of the pressing force by the user results in the slide member 531 moving in the second axial direction D2 back to the position of FIG. 5A, thereby returning the applicator 532 to the retracted position.

Figure 6:
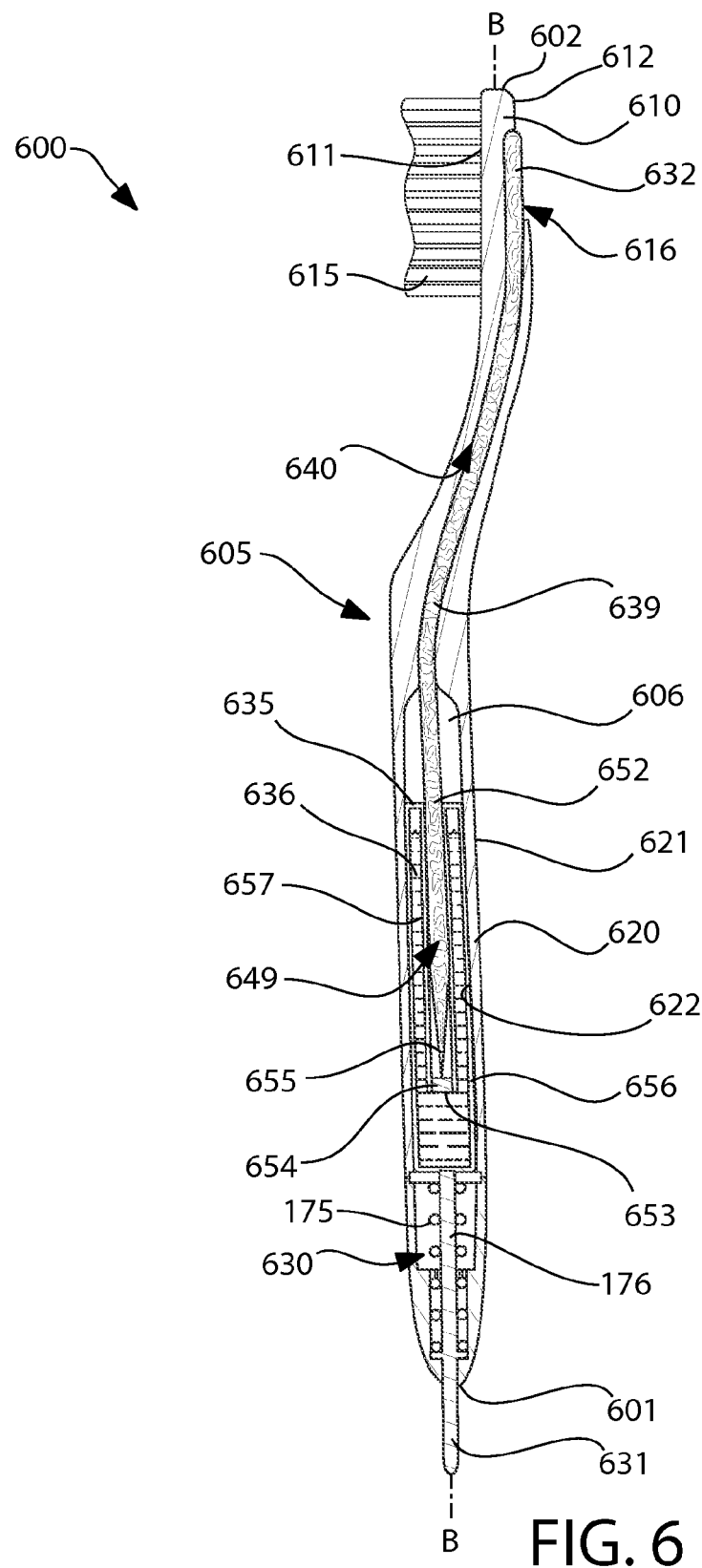
FIG. 6 is a longitudinal cross sectional view of a toothbrush according to a second embodiment of the present invention, wherein the reservoir housing is in a first position.
Figure 7:
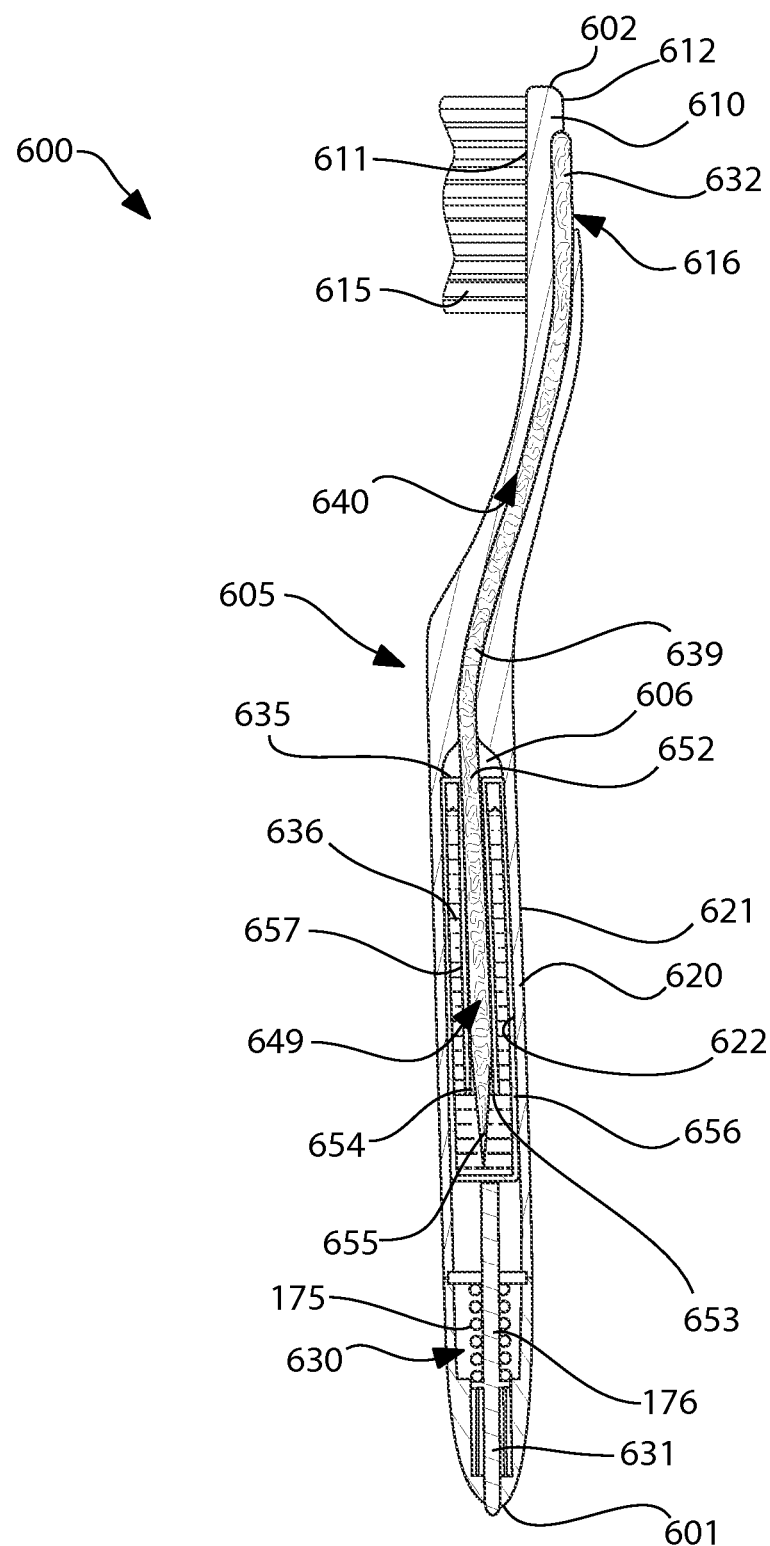
FIG. 7 is a longitudinal cross-sectional view of the toothbrush of FIG. 6, wherein the reservoir housing is in a second position.

Referring now to FIGS. 6 and 7, a second embodiment of a toothbrush 600 according to the present invention will be described. The toothbrush 600 has many features that are similar to or the same as features of the toothbrush 100. Thus, similar features will be similarly numbered with the exception that the 600-series of numbers will be used. It should be understood that features and components of the toothbrush 600 that are not described in detail herein are the same as corresponding features and components of the toothbrush 100.

The toothbrush 600 comprises a body 605 having a handle 620 and a head 610 coupled to an end of the handle 620. The oral care implement 600 extends from a proximal end 601 to a distal end 602 along a longitudinal axis B-B. The head 610 comprises a front surface 611 from which a plurality of tooth cleaning elements 615 extend and a rear surface 612 opposite the front surface 611. The body 605 comprises an outer surface 621 and an inner surface 622. The inner surface 622 of the body 605 defines an open area or internal cavity 606 within which a reservoir housing 635 is disposed. In the exemplified embodiment, the internal cavity 606 is formed within the handle 610 of the body 605. In other embodiments, the internal cavity 606 and/or the reservoir housing 635 can be partially or wholly located within the head, neck, handle or combinations thereof. The reservoir housing 635 contains an oral care fluid 636, such as any one of or a combination of the oral care fluids discussed above.

The toothbrush 600 comprises an applicator 632 that is mounted on the outer surface 621 of the body 605 so as to be affixed thereto. In the exemplified embodiment, the applicator 632 is affixed to the rear surface 612 of the head 610. The applicator 632, however, can be affixed to the outer surface 621 at other location on the body 605 in other embodiments. As with the toothbrush 100, the applicator 632 protrudes from the rear surface 612 of the head 610 and is partially disposed within a depression 616. Of course, the invention is not so limited and the depression 616 could be omitted if desired. Unlike the applicator 132 of the toothbrush 100, the applicator 632 does not move relative to the outer surface 621.

The body 605 comprises a channel 640 that extends from the internal cavity 606 to the applicator 632. The channel 640 can be take on any of the variations of the channel 140 discussed above. A fluid delivery member 639 is disposed within the channel 640 and extends from the applicator 632 and into the internal cavity 606. The fluid delivery member 639 is affixed to the applicator 632 and, thus, does not move relative thereto. In the exemplified embodiment, the fluid delivery member 639 and the applicator 632 are integrally formed as a single, unitary component. However, in other embodiments, the fluid delivery member 639 and the applicator 632 can be separate components that are subsequently mechanically coupled together. Both the applicator 632 and the fluid delivery member 639 are formed of a capillary material as discussed above for toothbrush 100 and are in fluid communication with each other so that oral care fluid can be delivered therethrough via capillary action. Conceptually, the fluid delivery member 639 can be considered a portion of the applicator 632, and vice versa, in certain embodiments.

The reservoir housing 635 is a U-shaped housing that fits snugly within the internal cavity 606 of the body 605. The reservoir housing 635 comprises an outer tubular wall 656 and an inner tubular wall 657, the outer tubular wall 656 circumferentially surrounding and being concentric with the inner tubular wall 657. The outer tubular wall 656 of the reservoir housing 635 is positioned adjacent to and in slidable contact with the inner surface 622 of the body 605. The inner tubular wall 657 forms a conduit 649 into the reservoir and to the oral care fluid 636. This conduit has an open top end 652 and an open bottom end 653. In the exemplified embodiment, a seal 654 is disposed within the conduit near the open bottom end 653 that can alternated between an open state and a closed state.

The fluid delivery member 639 extends into and is disposed within the conduit 649. Thus, the fluid delivery member 639 extends from the applicator 632, through the channel 640, into the internal cavity 606, and then into the conduit 649 of the reservoir housing 635. It should be understood that in certain embodiments the fluid delivery member 639 can be omitted altogether and the applicator 632 can extend directly into the conduit 649, depending on the size and position of the applicator 632.

The oral care implement 600 also comprises an actuator 630, such as the actuator described in detail above with regard to FIGS. 1-4 or FIGS. 5A and 5B. Of course, any actuator can be used within the scope of the present invention as discussed above. The actuator 630 is operably coupled to the reservoir housing 635 to move the reservoir housing 635 within the internal cavity 606. Specifically, the actuator 630 is able to move the reservoir housing 635 between a first position illustrated in FIG. 6 and a second position illustrated in FIG. 7. While the exemplified type of movement is translation, other types of movement can be used, including rotation.

When the reservoir housing 635 is in the first position (FIG. 6), the applicator 632 is removed from fluid communication with the oral care fluid 636 within the reservoir housing 635. In the exemplified embodiment, the applicator 632 is removed from fluid communication with the oral care fluid 636 within the reservoir housing 635 due to the reservoir housing 635 being translated away from the fluid delivery member 639 so that the fluid delivery member 639 is no longer in contact with the oral care fluid 636 within the reservoir housing 635.

When the reservoir housing 625 is in the second position (FIG. 7), the applicator 632 is in fluid communication, either directly or indirectly via the fluid delivery member 639, with the oral care fluid 636 within the reservoir housing 635 so that the oral care fluid 636 is delivered to the applicator 632 via capillary action. In the exemplified embodiment, the applicator 632 is in indirect fluid communication with the oral care fluid 636 through the fluid delivery member 639. As a result, the oral care fluid 636 within the reservoir housing 635 is drawn into the fluid delivery member 639 via capillary action and then subsequently delivered to the applicator 632 via capillary action. In one embodiment, the delivery of the oral care fluid 636 from the reservoir housing 635 to the applicator 632 is achieved solely by capillary action.

The reservoir housing 635 is moved between the first and second positions via movement imparted by actuation of the actuator 630. As can be seen, movement of the reservoir housing between the first and second position is achieved through a mechanical coupling of the push member 631 to the reservoir housing 635. In the exemplified embodiment, the movement of the reservoir housing 635 between the first and second positions is achieved by translational movement along the longitudinal axis B-B in the first and second axial directions. More specifically, the reservoir housing 635 is translated in the first axial direction D1 (FIG. 5A) when moved from the first position to the second position and in the second axial direction D2 (FIG. 5A) when moved from the second position to the first position. The second axial direction D2 is opposite the first axial direction D1.

In the exemplified embodiment, the fluid delivery member 639 is affixed to the applicator 632. As a result, both the applicator 639 and the fluid delivery member 639 remain stationary (relative to the body 605) during actuation of the actuator 630 and movement of the reservoir housing 635. In certain other embodiments, the fluid delivery member 639 is affixed to the reservoir housing 635 and separable from the applicator 632. In such embodiments, the fluid delivery member 639 remains in fluid communication with the oral care fluid 636 within the reservoir housing 635 at all times and positions. As a result, the movement of the reservoir housing 635 between the first and second positions effectuated by the actuator 630 also moves the fluid delivery member 639 in conjunction therewith. During such movement, the fluid delivery member 639 is brought into and out of contact, and thus into and out of fluid communication, with the applicator 632, which remains stationary. Specifically, when the reservoir housing 635 is in the first position, the fluid delivery member 639 is spaced from and not in fluid communication with the applicator 632. However, when the reservoir housing 635 is in the second position, the fluid delivery member 639 is in contact with and in fluid communication with the applicator 632, thereby delivering the oral care fluid to the applicator 632 via capillary action.

In the exemplified embodiment in which the applicator 632 and the fluid delivery member 639 are affixed to one another, the fluid delivery member 639 comprises a distal free end 655. The distal free end 655 can be shaped to narrows or taper to form a tip if desired. When the reservoir housing 635 is in the first position (FIG. 6), the pliable seal 654 (if provided) is in a closed state and seals the bottom end 653 of the conduit 649. In this state, the distal free end 655 of the fluid delivery member 639 is located above the pliable seal 654. Thus, when the reservoir housing 635 is in the first position, the fluid delivery member 639 is not in contact with the oral care fluid 636 within the reservoir housing 635. However, when the reservoir housing 635 is moved from the first position into the second position, the distal free end 655 of the fluid delivery member 639 penetrates the pliable seal 654 and passes through the open bottom end 653 and into contact with the oral care fluid 636 contained therein. In the second position, the fluid delivery member 639 is in fluid communication with the oral care fluid 636, thereby drawings the oral care fluid 636 therein via capillary action. Subsequently, the absorbed oral care fluid 636 will flow through the fluid delivery member 639 and into the applicator 632 via further capillary action. In the second position, the distal end 655 is preferably in contact with the floor of the reservoir 635 so as to be able to absorb all of the oral care fluid 636 therein via capillary action. When the reservoir housing 635 is returned to the first position, the fluid delivery member 639 withdrawn back through the pliable seal 654. The pliable seal 654 automatically returns to the closed state once the fluid delivery member 639 is fully withdrawn to seal the oral care fluid 636 within the reservoir housing 635.

In one embodiment of the present invention, the applicator 632 and/or the fluid delivery member 639 can be designed to have an adsorbent volumetric capacity that corresponds to a recommended single volumetric dose of the oral care fluid 636. Thus, the reservoir 635 can be positioned into the second position so that the fluid delivery member 639 and applicator 632 can become saturated with the oral care fluid 636. Then, prior to use of the oral care implement 600, the reservoir housing 635 can be moved to the first position, in which the applicator 632 is removed from fluid communication with the oral care fluid 636. The oral care implement 600 can then be used while the reservoir housing 635 is in the first position. As such, only the oral care fluid 636 that is already absorbed into the applicator 632 can be applied to the user's oral cavity. This can prevent overdosing on the oral care fluid 636 and ensure that a proper dosage is used.

Figure 8:
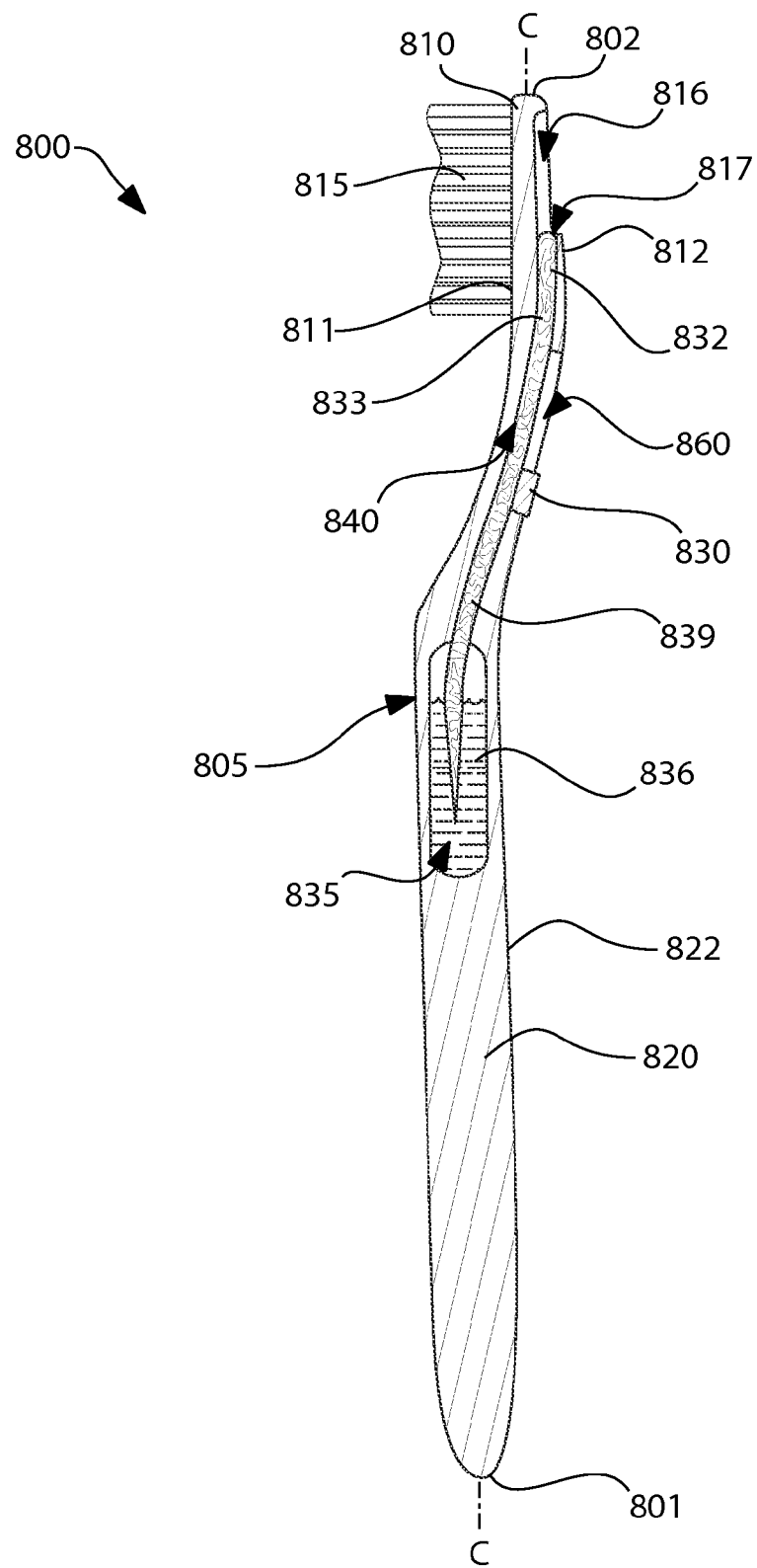
FIG. 8 is a longitudinal cross-sectional view of a toothbrush according to a third embodiment of the present invention, wherein the applicator is in a retracted position.
Figure 9:
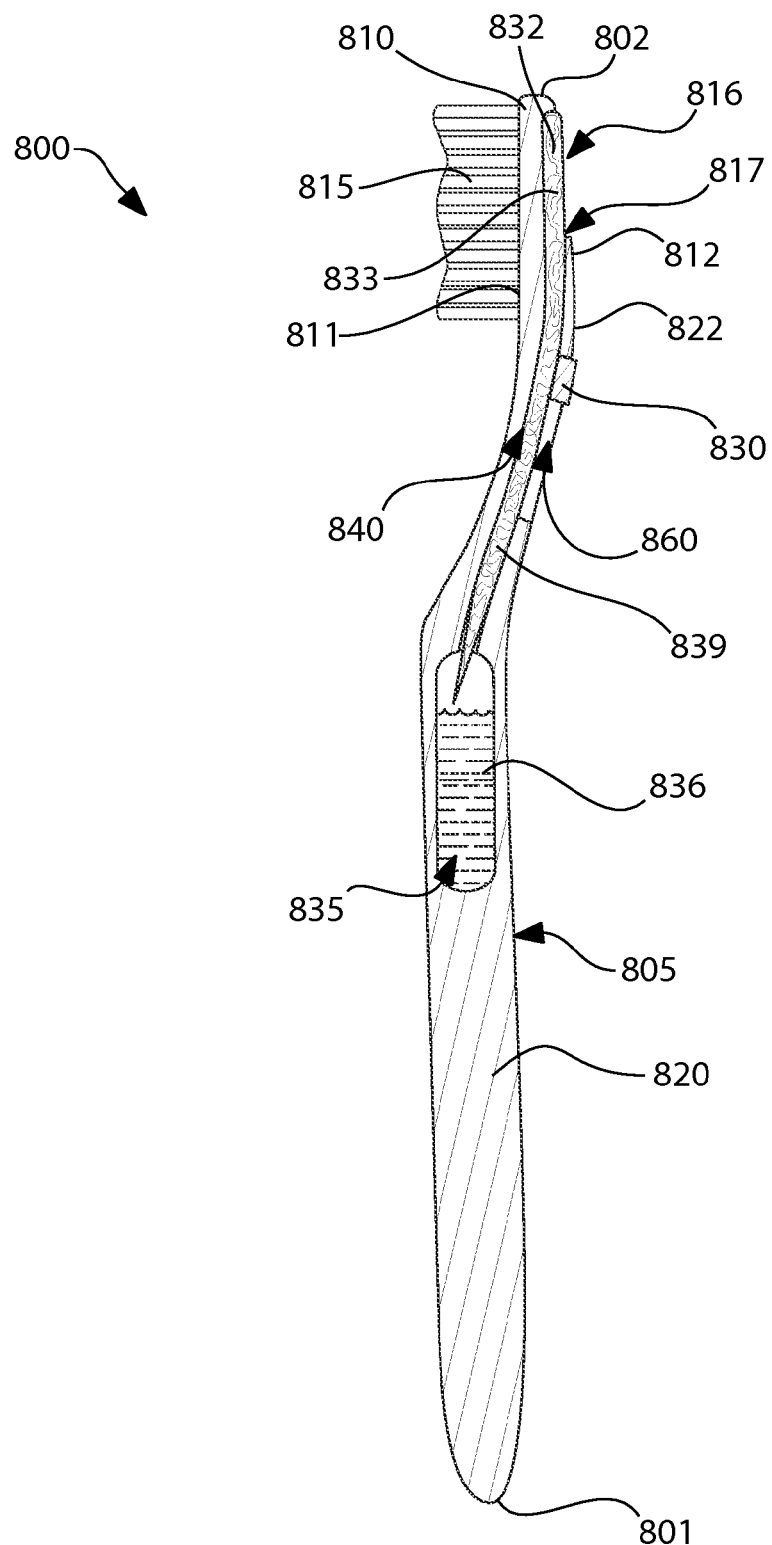
FIG. 9 is a longitudinal cross-sectional view of the toothbrush of FIG. 8, wherein the applicator is in a protracted position.

Referring now to FIGS. 8 and 9, a third embodiment of a toothbrush 800 according to the present invention will be described. The toothbrush 800 has many features that are similar to or the same as features of the toothbrushes 100 and 600 described above. Thus, those similar features will be similarly numbered with the exception that numbers from the 800-series will be used for describing the toothbrush 800. It should be understood that features and components of the toothbrush 800 that are not described in detail herein are the same as corresponding features and components of the toothbrushes 100, 600.

The toothbrush 800 extends from a proximal end 801 to a distal end 802 along a longitudinal axis C-C. The oral care implement 800 generally comprises a body 805 having a handle 820 and a head 810, the head 810 coupled to an end of the handle 820. The head 810 comprises a front surface 811 with a plurality of tooth cleaning elements 815 extending therefrom and a rear surface 812 that is opposite the front surface 811.

The rear surface 812 of the head 810 comprises an opening 817 that is the termination of the channel 840 in the outer surface 822 of the body 805. The body 805 comprises an internal reservoir 835 that contains an oral care fluid 836 therein. In the exemplified embodiment, the reservoir 835 is located within the handle 810 of the toothbrush 800 but can positioned elsewhere as described above. The channel 840 extends from the reservoir 835, to the opening 817. Thus, the channel 840 forms a passageway from the reservoir 835 to the opening 817, and hence also to the depression 816 as discussed above.

The oral care implement 800 also comprises an applicator 832 that is formed of a capillary material, such as any of the capillary materials discussed above. As such, the applicator 832 is capable of absorbing fluidic material, such as the oral care fluid 836, via capillary action when the applicator 832 is in fluid communication with the oral care fluid 836. The oral care implement also comprises an actuator 830. In the exemplary embodiment the actuator 830 is a slide button that is located on the body 805. Of course, the actuator 830 can take on other structural arrangements and configurations as discussed above. In the exemplified embodiment, the actuator 830 is operably coupled to the applicator 832 in order to move the applicator 832 between a protracted position (FIG. 9) in which a portion 833 of the applicator 832 protrudes from the opening 817 and a retracted position (FIG. 8) in which the portion 833 of the applicator 832 is retracted into the channel 840 via the opening 817.

Movement of the applicator 832 between the protracted and retracted positions is a result of sliding the actuator 830 in the first and second axial directions D1, D2. The body 805 comprises a slot 860 within which the actuator 830 is able to slide. As such, the actuator 830 can slide within the slot 860 in the first and second axial directions D1, D2 in order to move the applicator 832 between the retracted and protracted positions. Specifically, the actuator 830, and hence also the applicator 832 is translated in the first axial direction D1 when moving the applicator 832 from the retracted position to the protracted position and in the second axial direction D2 when moving the applicator 832 from the protracted position to the retracted position. The applicator 832 remains mounted to the body 805 of the oral care implement 800 when the applicator 832 is in both the protracted and retracted positions.

As can be seen from FIG. 8, when the applicator 832 is in the retracted position, the applicator 832 is in fluid communication with the oral care fluid 836 within the reservoir 835. When the applicator is in the retracted position, no portion of the applicator 832 protrudes from the opening 817. Of course, the invention is not so limited and a small portion of the applicator 832 may protrude from the opening 817 when the applicator 832 is in the retracted position in certain embodiments. In the retracted position, the oral care fluid 836 is delivered to the applicator 832 via capillary action and the applicator 832 is protected against external contaminants. In the protracted position, the applicator 832 is removed from fluid communication with the oral care fluid 836 and the applicator 832 is exposed to the external environment by protruding through the opening 817 and into the depression 816. The applicator 832 is at least partially disposed within the channel 840 in both the protracted and retracted positions to provide structural integrity of the applicator 832 during use.

As with the toothbrushes 100, 600, the toothbrush 800 may also comprises a fluid delivery member 839 comprised of a capillary material. In the exemplified embodiment, the fluid delivery member 839 is integrally formed with the applicator 832 such that they appear to be a single, solitary unit. Of course, the invention is not so limited and in certain other embodiments the fluid delivery member 839 and the applicator 832 are separate components that are affixed to one another at a later stage. The fluid delivery member 839 extends between the reservoir 835 and the applicator 832 to effectuate the fluid communication between the applicator 832 and the oral care fluid 836 when the applicator 832 is in the retracted position. Of course, the fluid delivery member 839 could be omitted if desired.

In embodiments that include a fluid delivery member 839, the delivery member 639 can be conceptually considered as a portion of the applicator 832, and vice versa. Actuation of the actuator 830 will slide the delivery member 839 within the channel 840, which will in turn move the applicator 832 between the protracted and retracted positions. In certain other embodiments not illustrated herein, the delivery member 839 can be affixed to the reservoir 835 and separable from the applicator 832, as discussed above regarding the toothbrush 600.

As can be seen in FIG. 9, when the applicator 832 is in the protracted position, the portion 833 of the applicator 832 is located on the rear surface 812 of the head 810. More specifically, when in the protracted position, the portion 833 of the applicator 832 is at least partially positioned within and protrudes from the depression 816 on the rear surface 812 of the head 810.

Similar to the toothbrush 600, the applicator 832 of the toothbrush 800 can be designed to have an adsorbent volumetric capacity that corresponds to a single volumetric dose of the oral care fluid 836. As such, the applicator 832 can be positioned in the retracted position so that the applicator 832 is in fluid communication with the oral care fluid 836. In this retracted position, the capillary material of the applicator 832 will soak up a specific amount of the oral care fluid 836 that properly corresponds to a single dose of the oral care fluid 836. The amount of the oral care fluid 836 that corresponds to a single dose can vary depending on the oral care fluid used and many other factors including the age of the user, the weight of the user, the particular problem or health issue that the user is attempting to resolve, and the like. When the applicator 832 is moved from the retracted position to the protracted position, the single dose of the oral care fluid 836 will dispense out of the applicator 832 during use.

The oral care implement 800 is advantageous in that the applicator 832 can be disconnected from the reservoir 835 during periods of use. This helps to control the dose delivered because the volume of the oral care fluid 836 contained within the applicator 832 is the only portion of the oral care fluid 836 delivered during a single use. Furthermore, the oral care implement 800 provides a further hygienic improvement in that the applicator 832 can be completely rinsed with water or some other cleaning solution without impacting the level of the oral care fluid 836 in the reservoir 835.

Figure 10:
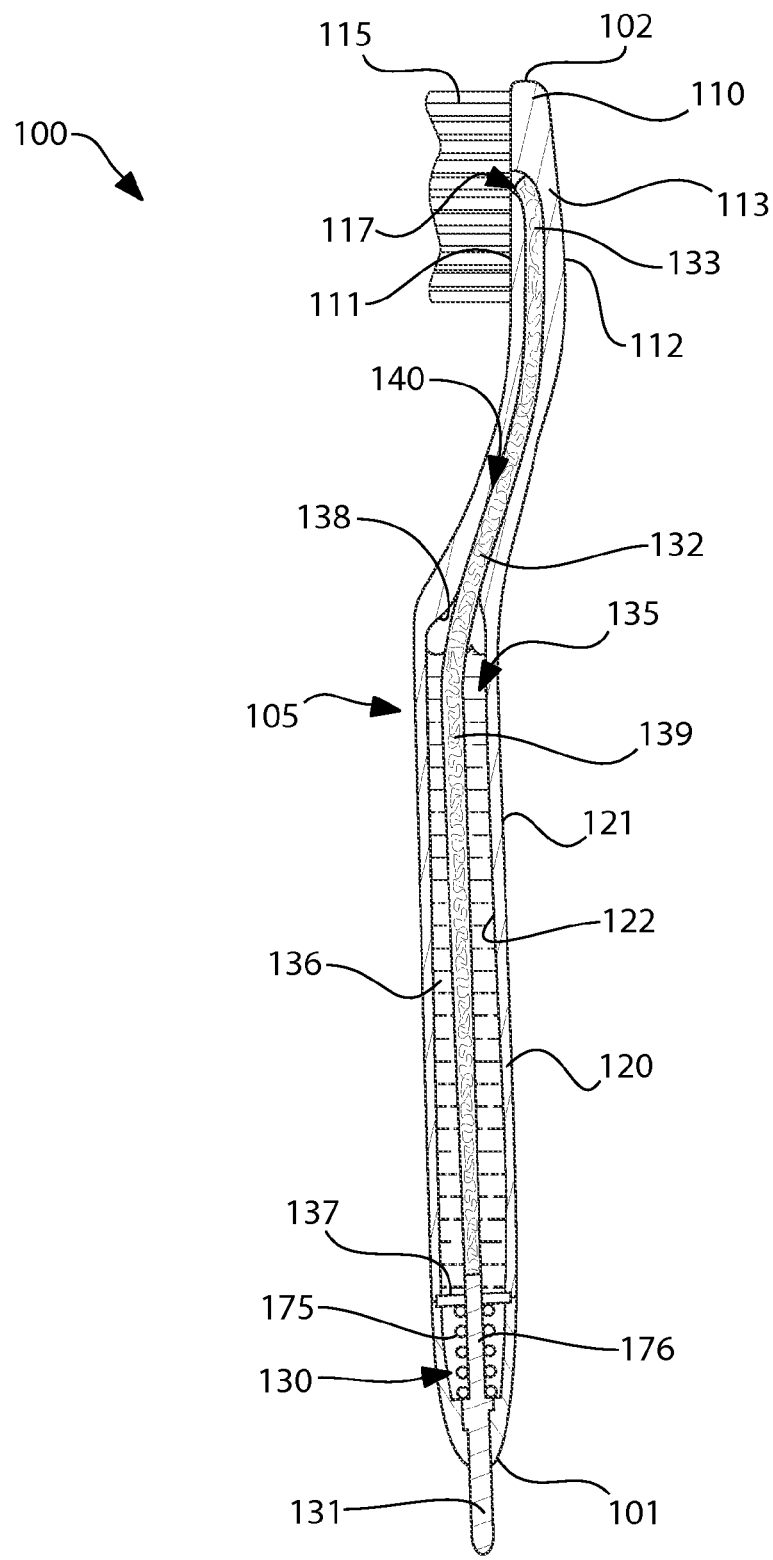
FIG. 10 is a longitudinal cross-sectional view of a toothbrush according to a fourth embodiment of the present invention, wherein the applicator is in a retracted position on the front surface of the head.
Figure 11:
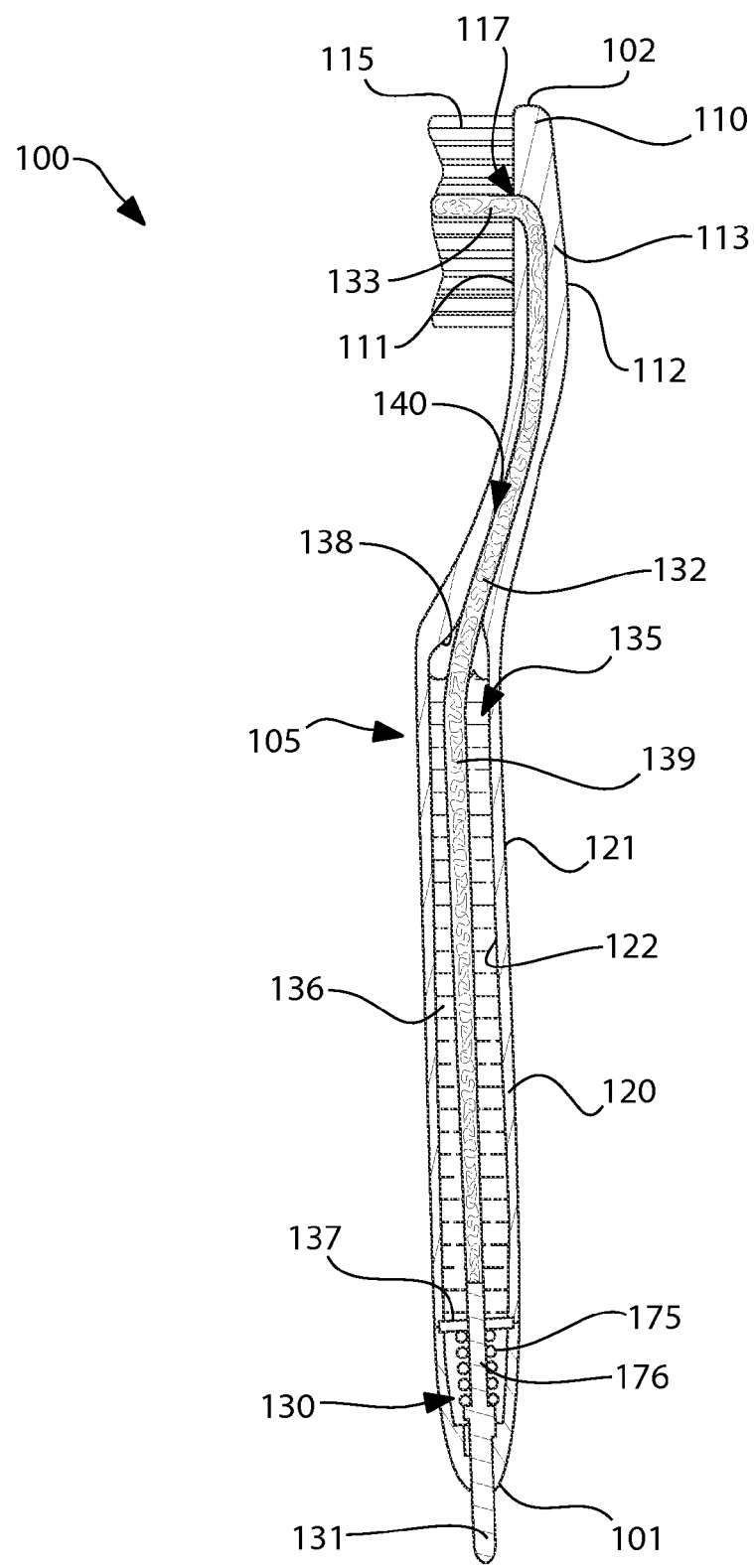
FIG. 11 is a longitudinal cross-sectional view of the toothbrush of FIG. 8, wherein the applicator is in a protracted position extending from front surface of the head.

Referring to FIGS. 10 and 11, an embodiment of the toothbrush 100 will be described where the applicator 132 extends from the front surface 111 of the head 110 rather than from the rear surface 112 of the head 110 when the applicator 132 is in the protracted position. Thus, all of the reference numerals used in FIGS. 1-4 are equally applicable to the description of FIGS. 10 and 11 that follows. In the embodiment illustrated in FIGS. 10 and 11, the channel 140 extends from the reservoir 135 to an opening 117 on the front surface 111 of the head 110. The toothbrush 100 has an applicator 132 that is disposed within the reservoir 135 and extends through the channel 140. The toothbrush 100 has an actuator 130 that is capable of moving the applicator 132 between a retracted position and a protracted position. When the applicator 132 is in the protracted position (FIG. 11), a portion 133 of the applicator 132 is exposed for application of an oral care fluid 136 to a user's oral cavity. Referring solely to FIG. 10, when the applicator 132 is in the retracted position, the portion 133 of the applicator 132 is withdrawn within the opening 117 and thus nests within the channel 140, thereby providing a storage position in which the applicator 132 is protected from excess evaporation and contamination during periods of non-use.

As noted above, in the embodiment illustrated in FIGS. 10 and 11, the opening 117 is located on the front surface 111 of the head 110. As such, when the applicator 132 is in the protracted position, the portion 133 of the applicator 132 protrudes through the opening 117 and extends from the front surface 111 of the head 110. Furthermore, a plurality of tooth cleaning elements 115, which may be considered a field of tooth cleaning elements, also extend from the front surface 111 of the head 110. Thus, when the actuator 130 is in the protracted position, the portion 133 of the applicator 132 extends from the front surface 111 of the head 110 and is located within the field of cleaning elements. In the exemplified embodiment, the portion 133 of the applicator 132 extends from the front surface 111 of the head 110 the same distance as the tooth cleaning elements 115. However, the invention is not to be so limited and in certain other embodiments the portion 133 of the applicator 132 may extend from the front surface of the head 110 a greater or lesser distance than the tooth cleaning elements 115. When the applicator 132 is in the protracted position, the portion 133 of the applicator 132 will deliver the oral care fluid 136 to the user's teeth, gums and other oral surfaces as has been described in detail above.

In alternative embodiments, the opening 117 is located on other portions of the head 110 or other portions of the toothbrush 100. Thus, in these embodiments, the portion 133 of the applicator 132 protrudes through other portions of the head 110 or other portions of the toothbrush 100. For example, in one embodiment, the opening 117 is located on a side portion of the head 110 or a side portion of the toothbrush 100.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

While the foregoing description and drawings represent the exemplary embodiments of the present invention, it will be understood that various additions, modifications and substitutions may be made therein without departing from the spirit and scope of the present invention as defined in the accompanying claims. In particular, it will be clear to those skilled in the art that the present invention may be embodied in other specific forms, structures, arrangements, proportions, sizes, and with other elements, materials, and components, without departing from the spirit or essential characteristics thereof. One skilled in the art will appreciate that the invention may be used with many modifications of structure, arrangement, proportions, sizes, materials, and components and otherwise, used in the practice of the invention, which are particularly adapted to specific environments and operative requirements without departing from the principles of the present invention. The presently disclosed embodiments are therefore to be considered in all respects as illustrative and not restrictive, the scope of the invention being defined by the appended claims, and not limited to the foregoing description or embodiments. For example, in certain embodiments, the delivery of the oral care fluid from the reservoir to the applicator can be supplemented by mechanical action if desired.

What is claimed is:

1. A toothbrush having a longitudinal axis comprising:
   a body comprising a handle, a head coupled to a distal end of the handle, and an internal reservoir containing an oral care fluid;
   a channel in the body extending from the reservoir to an opening in an outer surface of the body;
   an applicator comprising a capillary material;
   an actuator operably coupled to the applicator to move the applicator between: (1) a protracted position in which a portion of the applicator protrudes from the opening; and (2) a retracted position in which the portion of the applicator is retracted into the channel via the opening; and
   wherein the applicator is in fluid communication with the oral care fluid within the reservoir in both the protracted position and the retracted position so that the oral care fluid is delivered to the applicator via capillary action.

2. The toothbrush according to claim 1 wherein the applicator is at least partially disposed within the channel in both the protracted position and the retracted position.

3. The toothbrush according to claim 1 further comprising a fluid delivery member comprising a capillary material, the fluid delivery member extending between the reservoir and the applicator to effectuate the fluid communication between the applicator and the oral care fluid within the reservoir.

4. The toothbrush according to claim 3 wherein the delivery member is affixed to the applicator, wherein actuation of the actuator slides the delivery member within the channel to move the applicator between the protracted position and the retracted position.

5. The toothbrush according to claim 1 wherein when the applicator is in the protracted position, the portion of the applicator is located on a rear surface of the head.

6. The toothbrush according to claim 5 further comprising a plurality of tooth cleaning elements extending from a front surface of the head, the front surface of the head being opposite the rear surface of the head.

7. The toothbrush according to claim 5 wherein a depression is formed in the rear surface of the head, the portion of the applicator being at least partially disposed within the depression when the applicator is in the protracted position.

8. The toothbrush according to claim 5 wherein the portion of the applicator protrudes from the rear surface of the head when the applicator is in the protracted position.

9. The toothbrush according to claim 1 wherein the actuator comprises a push member that protrudes from a proximal end of the handle, wherein movement of the push member in a first axial direction moves the applicator from the retracted position to the protracted position and movement of the push member in a second axial direction opposite the first axial direction moves the applicator from the protracted position to the retracted position.

10. The toothbrush according to claim 1 wherein the actuator comprises a resilient member that biases the applicator into the retracted position.

11. The toothbrush according to claim 10 wherein the actuator comprises an interference lock that is activated so as to maintain the applicator in the protracted position upon a first movement of the push member in the first axial direction, the interference lock being deactivated so as to allow the applicator to be biased into the retracted position upon a second movement of the push member in the first axial direction.

12. The toothbrush according to claim 11 wherein the interference lock comprises a slot, a flange and a cam surface for rotating one of the flange or the slot into and out of axial alignment with the other one of the flange or the slot.

13. The toothbrush according to claim 1 wherein the applicator is translated in a first axial direction when moved from the retracted position to the protracted position and in a second axial direction when moved from the protracted position to the retracted position, the second axial direction being opposite the first axial position.

14. The toothbrush according to claim 1 wherein when the applicator is in the protracted position, the portion of the applicator extends from a front surface of the head.

15. The toothbrush according to claim 14 further comprising a field of tooth cleaning elements extending from the front surface of the head, the applicator positioned within the field of tooth cleaning elements when the applicator is in the protracted position.

16. A toothbrush having a longitudinal axis comprising:
   a body comprising a handle, a head coupled to a distal end of the handle, and an internal reservoir containing an oral care fluid;
   a channel in the body extending from the reservoir to an opening in an outer surface of the body;
   an applicator comprising a capillary material;
   an actuator operably coupled to the applicator to move the applicator between: (1) a protracted position in which a portion of the applicator protrudes from the opening; and (2) a retracted position in which the portion of the applicator is retracted into the channel via the opening; and
   wherein the applicator is in fluid communication with the oral care fluid within the reservoir in the retracted position so that the oral care fluid is delivered to the applicator via capillary action and removed from fluid communication with the oral care fluid within the reservoir in the protracted position.

17. A toothbrush having a longitudinal axis comprising:
a body comprising a handle, a head coupled to a distal end of the handle, and an internal cavity;
a reservoir housing disposed within the internal cavity of the body and containing an oral care fluid;
an applicator comprising a capillary material affixed to an outer surface of the body;
a channel in the body extending from the internal cavity to the applicator;
an actuator operably coupled to the reservoir housing for moving the reservoir housing within the internal cavity between: (1) a first position in which the applicator is removed from fluid communication with the oral care fluid within the reservoir housing; and (2) a second position in which the applicator is in fluid communication with the oral care fluid within the reservoir housing so that the oral care fluid is delivered to the applicator via capillary action.

18. The toothbrush according to claim 17 further comprising a fluid delivery member comprising a capillary material, the fluid delivery member extending between the oral care fluid in the reservoir housing and the applicator to effectuate the fluid communication between the applicator and the oral care fluid within the reservoir when the reservoir housing is in the second position.

19. The toothbrush according to claim 18 wherein the delivery member is affixed to the applicator, wherein actuation of the reservoir housing brings the delivery member into and out of fluid coupling with the applicator.

20. The toothbrush according to claim 18 wherein the delivery member is affixed to the reservoir housing, wherein actuation of the reservoir housing brings the delivery member into and out of fluid coupling with the oral care fluid in the reservoir housing.

21. The toothbrush according to claim 17 wherein the actuator comprises a push member that protrudes from a proximal end of the handle, wherein movement of the push member in a first axial direction moves the reservoir housing from the first position to the second position and movement of the push member in a second axial direction opposite the first axial direction moves the reservoir housing from the second position to the first position.

22. The toothbrush according to claim 17 wherein the reservoir housing is translated in a first axial direction when moved from the first position to the second position and in a second axial direction when moved from the second position to the first position, the second axial direction being opposite the first axial position.

23. The toothbrush according to claim 17 wherein the applicator is affixed to a rear surface of the head.

24. The toothbrush according to claim 17 wherein the reservoir housing comprises an inner tubular wall and an outer tubular wall circumferentially surrounding the inner tubular wall, the inner tubular wall forming a conduit to the oral care fluid.

25. The toothbrush according to claim 24 further comprising a pliable seal positioned within the conduit.

26. The toothbrush according to claim 17 wherein the applicator extends from a front surface of the head.

* * * * *